(12) United States Patent
Arizti et al.

(10) Patent No.: US 7,654,993 B2
(45) Date of Patent: Feb. 2, 2010

(54) ABSORBENT ARTICLES WITH COMFORTABLE ELASTICATED LAMINATES

(75) Inventors: Blanca Arizti, Frankfurt (DE);
Ekaterina Anatolyevna Ponomarenko, Bad Soden (DE); Simone Seeboth, Schwalbach (DE); Gemma Baquer-Molas, Schwalbach (DE)

(73) Assignee: The Procter and Gamble Company, Cincinnati, OH (US)

( * ) Notice: Subject to any disclaimer, the term of this patent is extended or adjusted under 35 U.S.C. 154(b) by 103 days.

(21) Appl. No.: 11/582,189

(22) Filed: Oct. 17, 2006

(65) Prior Publication Data

US 2007/0093771 A1 Apr. 26, 2007

(51) Int. Cl.
A61F 13/15 (2006.01)
A61F 13/20 (2006.01)

(52) U.S. Cl. .............. 604/385.27; 604/385.28; 604/385.22

(58) Field of Classification Search ......... 604/367, 604/381–382, 385.01, 385.24–385.28
See application file for complete search history.

(56) References Cited

U.S. PATENT DOCUMENTS

| | | | |
|---|---|---|---|
| 3,911,173 A | 10/1975 | Sprague, Jr. | |
| 4,785,996 A | 11/1988 | Ziecker et al. | |
| 4,842,666 A | 6/1989 | Wierenicz | |
| 4,940,464 A | 7/1990 | Van Gompel et al. | |
| 4,988,344 A | 1/1991 | Reising et al. | |
| 4,988,345 A | 1/1991 | Reising | |
| 5,092,861 A | 3/1992 | Nomura et al. | |
| 5,246,433 A | 9/1993 | Hasse et al. | |
| 5,322,729 A | 6/1994 | Heeter et al. | |
| 5,342,342 A * | 8/1994 | Kitaoka | 604/385.19 |
| 5,569,234 A | 10/1996 | Buell et al. | |
| 5,571,096 A | 11/1996 | Dobrin et al. | |
| 5,607,760 A | 3/1997 | Roe | |
| H1670 H | 7/1997 | Aziz et al. | |
| H1732 H | 6/1998 | Johnson | |
| 5,865,823 A | 2/1999 | Curro | |
| 5,876,753 A | 3/1999 | Timmons et al. | |
| 5,888,591 A | 3/1999 | Gleason et al. | |
| 5,938,648 A | 8/1999 | LaVon et al. | |
| 6,045,877 A | 4/2000 | Gleason et al. | |
| 6,120,487 A | 9/2000 | Ashton | |
| 6,120,489 A | 9/2000 | Johnson et al. | |
| 6,482,191 B1 | 11/2002 | Roe et al. | |
| 2003/0004489 A1 * | 1/2003 | Ashton et al. | 604/385.25 |
| 2005/0095942 A1 | 5/2005 | Mueller et al. | |

FOREIGN PATENT DOCUMENTS

| | | | |
|---|---|---|---|
| EP | 1 072 243 A2 * | 1/2001 | |
| WO | WO 95/16746 A1 | 6/1995 | |
| WO | WO 96/03501 A1 | 2/1996 | |

* cited by examiner

*Primary Examiner*—Michele Kidwell
(74) *Attorney, Agent, or Firm*—John G. Powell; William E. Gallagher

(57) ABSTRACT

An absorbent article that includes a component with an elastic laminate portion, which provides y-direction elongation. The elastic laminate portion is a support sheet and an elastic material, together forming a laminate portion of the component. The elastic laminate portion has zones, each with a different degree of maximum elongation. The zones also have different wrinkle heights and/or densities, such that one or more zones are created that cause less or no pressure marks, whilst overall an excellent force profile is maintained, resulting in well performing, comfortable to wear absorbent articles.

8 Claims, 9 Drawing Sheets

ABSORBENT ARTICLES WITH COMFORTABLE ELASTICATED LAMINATES

FIELD OF THE INVENTION

This invention relates to absorbent articles comprising a component that comprises an elastic laminate with elongation (stretch) along a first direction, comprising a support sheet and an elastic material and zones wherein each zone has a different degree of maximum elongation, different wrinkle heights and/or different wrinkle densities.

BACKGROUND TO THE INVENTION

Absorbent articles such as infant diapers, training pants and adult incontinence garments typically comprise elastic leg cuffs and or barrier cuffs to reduce leakage of exudates from the article. Often, they also comprise an elasticated waist band to improve the fit and comfort when the wearer is moving. A certain type of diapers for feces isolation comprises (also) a topsheet with a large opening with there along elastic bands to ensure correct alignment of the topsheet and the opening with the anus of the user, and to thus ensure optimum reception and isolation of the feces under the topsheet.

These elasticated portions of such articles typically comprise a laminate of an elastic material attached to a non-elastic sheet, such as a plastic film, or nonwoven material, obtained by attaching the elastic material in stretched state to the sheet. The resulting laminate thus comprises in unstretched, contracted state and in partially stretched state a surplus of sheet material that forms wrinkles.

Such elasticated portions of the diaper may be uncomfortable in use, due to the pressure of the elastic portions on the skin and/or due to rubbing of the wrinkled elasticated portions over the skin.

The inventors have also found that even if the user does not experience the elasticated portions as uncomfortable, the red skin marks caused by the elasticated portions may still be perceived by the care taker as uncomfortable for the user.

The inventors have also found that in use the most stringent problem is the presence of pressure marks close to the sensitive areas of the users, e.g., the genitals. They found surprisingly that provided the pressure marks are reduced on the skin close to the genitals, the diaper will be (perceived to be) more comfortable.

The inventors have found that by providing elastic portions, e.g., elasticated leg cuffs, in the absorbent article (diaper), that have a (small) zone with only a minor degree of elastication, or no elastication at all, that correspond in use with these sensitive areas, and that have larger zones with higher degrees of elastication, an absorbent article (e.g., diaper) is obtained that still maintain an excellent elastic profile and performance and at the same type has a highly reduced or no pressure mark problem and that is more comfortable in use.

SUMMARY OF THE INVENTION

The invention relates to a disposable absorbent article, such as, for example, a diaper, training pants or adult incontinence garment, comprising a component with an elastic laminate portion, being an elastic material attached to a supporting material or sheet, said component and elastic laminate portion being elastically stretchable in a first direction (e.g., y-direction), whereby said elastic laminate portion has an absolute contracted length $L_c$ and a fully stretched absolute length $L_s$, and whereby said elastic laminate portion can be elongated with a maximum elongation $\epsilon$ of at least 0.6, and whereby:

said laminate portion has (in y-direction) zones with different maximum elongation, including a first zone with an absolute contracted length $L_{czone1}$ and an absolute stretched length $L_{szone1}$ and a maximum elongation $\epsilon_{zone1}$ of less than 50% of $\epsilon$, and a second zone with an absolute contracted length $L_{czone2}$ and an absolute stretched length $L_{szone2}$ and with a maximum y-direction elongation $\epsilon_{zone2}$ of more than $\epsilon$, said first zone and second zone having an absolute contracted length $L_{czone1}$ and $L_{czone2}$ of at least 2 cm.

The invention also relates to a disposable absorbent article comprising a component that comprises an elastic laminate portion, being an elastic material attached to a supporting sheet, said component and laminate portion being elastically stretchable in a first direction (y-direction), and said elastic laminate portion having a fully stretched absolute length $L_s$ and an absolute contracted length $L_c$, and whereby said elastic laminate portion can be elongated with an elongation $\epsilon$ of at least 0.6 or at least 0.8, whereby:

said elastic laminate portion has zones (1, 2) (in y-direction) of different maximum elongation, having at least a first zone with an absolute contracted length $L_{czone1}$ and an absolute stretched length $L_{szone1}$ and a maximum y-direction elongation $\epsilon_{zone1}$ and a second zone with an absolute contracted length $L_{czone2}$ and an absolute stretched length $L_{szone2}$ and with a maximum elongation $\epsilon_{zone2}$, and whereby said first zone and said second zone each have an absolute contracted length $L_{czone1}$ of at least 2 cm, and whereby at a partial elongation $\epsilon$=0.5, a) said elastic laminate portion has wrinkles with an average wrinkle height (in z-direction) $H_w$, and said first zone has no wrinkles or wrinkles with an average wrinkle height $H_{wzone1}$ of less than 50% of $H_w$, and/or b) said elasticated laminate portion has a wrinkle density $D_w$ (wrinkles per cm) and said first zone has a wrinkle density $D_{wzone1}$ of 0 or of less than 50% of $D_w$.

The elastic laminate portion may comprise at least three zones (1, 2, 3) where the first zone is positioned between the second and third zone (3) (in the direction of stretch). The first zone may be positioned in the crotch region of the article, or in the front 50% of the article. The contracted length of the second zone may be more than the contracted length of the first zone. Optionally, the elastic laminate portion may comprise on either or both longitudinal end (an) attachment portion (s) (4) of less than 1.5 cm long preferably less than 1 cm long, where the elastic laminate portion has a reduced elongation potential, e.g., like the first zone.

DETAILED DESCRIPTION

"Absorbent article" refers to wearable devices, which absorb and/or contain liquid, and more specifically, refers to devices, which are placed against or in proximity to the body of the wearer to absorb and contain the various exudates discharged from the body. As used herein, the term "diaper" refers to an absorbent article generally worn by infants and incontinent people about the lower torso.

"Y-direction elongation or stretch" as used herein means that the laminate portion (10) has, as a whole, an elongation or stretch in an average direction, that is herein referred to as "y-direction." The y-direction may be within 45 degrees of the longitudinal axis or line parallel thereto of the elastic laminate portion (10).

"Absolute fully stretched length" is the length of the elastic laminate portion (10) when said component (11) or portion (10) is stretched in y-direction as set out herein to its maximum length.

"Absolute contracted length" is the length of the elastic laminate portion (10), when no stretching force is applied to it, e.g., when it is in relaxed state, flat on a surface.

The "z-direction" is perpendicular to the y-direction and substantially in the direction of the wrinkle height in the laminate, and is herein also referred to as the height or thickness dimension.

The "x-direction" is perpendicular to both the x- and y-directions.

As used herein, the term "void space" is a cavity sized to accept and contain bodily exudates such as fecal material, present in at least the relaxed state of the article.

As used herein, "elastic" means, that the item is extendible or stretchable by application of a force in a certain direction and returns to at least 80% of its original length but to less than 150% of its original length in that direction, and typically to about its original size, after the stretching force is released.

As used herein, "along" means at least partially parallel and in close proximity or even in contact with.

As used herein "attached" includes "directly attached" and "indirectly attached." Each embodiment defined by certain properties or dimension for which a value is defined herein is to be understood to include embodiments with functional equivalent properties or dimensions, e.g., a dimension of 0.5 cm has to be understood as meaning "about 0.5 cm".

The disposable absorbent article of the invention may be a sanitary napkin, panty-liner, or a diaper, i.e., an adult incontinence garment or baby or infant diaper (as shown in the FIGS. 1 to 5) or training or pull-up pants. The article comprises an elastic laminate portion (10), described herein, and additional components, to have typically at least a backsheet (21), absorbent core and a core cover sheet or topsheet (20).

The absorbent article of the invention comprises at least one component comprising at least one elastic laminate portion (10), formed from an elastic material (12) and a supporting sheet material, that itself is typically not elastically stretchable, said elastic laminate portion (10) having at least stretch (elongation) along a first direction, e.g., y-direction, or only along said first or y-direction, as shown in the Figures. Thus, the invention embodies an absorbent article that comprises one or more components that each consists of such a laminate portion (10), and an article that contains one or more components that (each) comprise one or more of such a distinct or separate laminate portions (10).

If the components of the absorbent article are, for example, leg cuffs (25) or barrier cuffs (26) comprising or consisting of said elastic laminate portion (10), then the y-direction of the leg cuffs (25) or barrier cuffs (26) and said laminate portion(s) (10) are typically substantially parallel or on average parallel to the y-direction and y-axis of the article. When the component herein with the elastic laminate portion (10) is a waistband (24), then the longitudinal or y-direction of said waistband (24) and the elastic laminate portion (10) thereof may be perpendicular to the direction y-direction of the article.

Furthermore, each said component may comprise more than one of such laminate portions (10), which each may be identical in zones (1c, 2c), length and elongations thereof as referred to herein, or that may have different zones (1c, 2c), lengths and elongations thereof.

The component may consist of a supporting sheet and the elastic material (12) and optionally attachment means, but it may comprise additional elements. The supporting sheet may be a single sheet or it may comprise more than one sheet or layer, e.g., it may be a laminate of layers. It may be preferred that the supporting sheet itself is not elastically stretchable in the first direction of stretch, e.g., y-direction, or not elastically stretchable in any direction.

In one example of an embodiment of the present invention said component is a waist band (24), a leg cuff (25) or barrier cuff (26) of the absorbent article of the invention, as described herein below in more detail. However, the elastic laminates (10) of the present invention may also be useful in or as other parts of an absorbent article. The article may comprise at least two distinct and separate components, e.g., a pair of leg cuffs (25) with each comprising or consisting of the elastic laminate portion (10).

Figure 1:
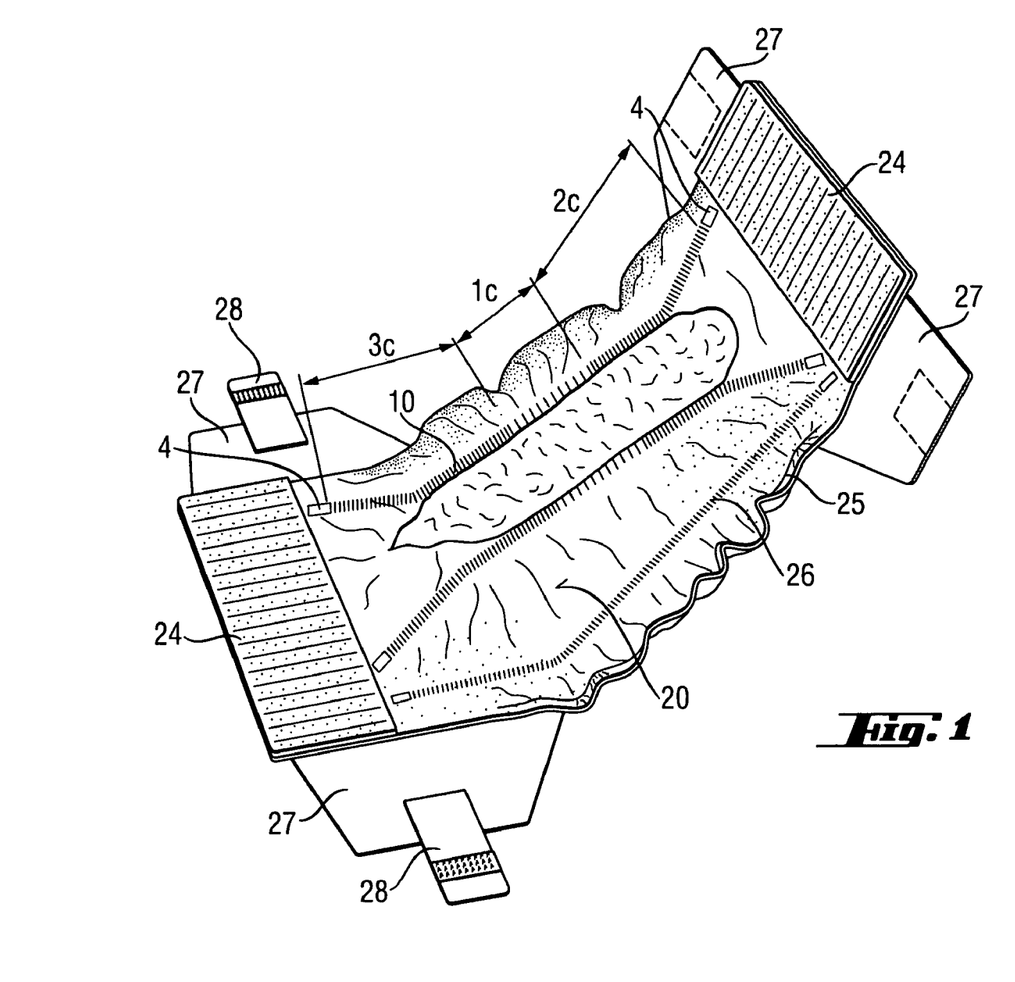
FIG. 1 shows a perspective view of an exemplary diaper of the present invention having a first zone (1c) with only very limited elongation potential.
Figure 2:
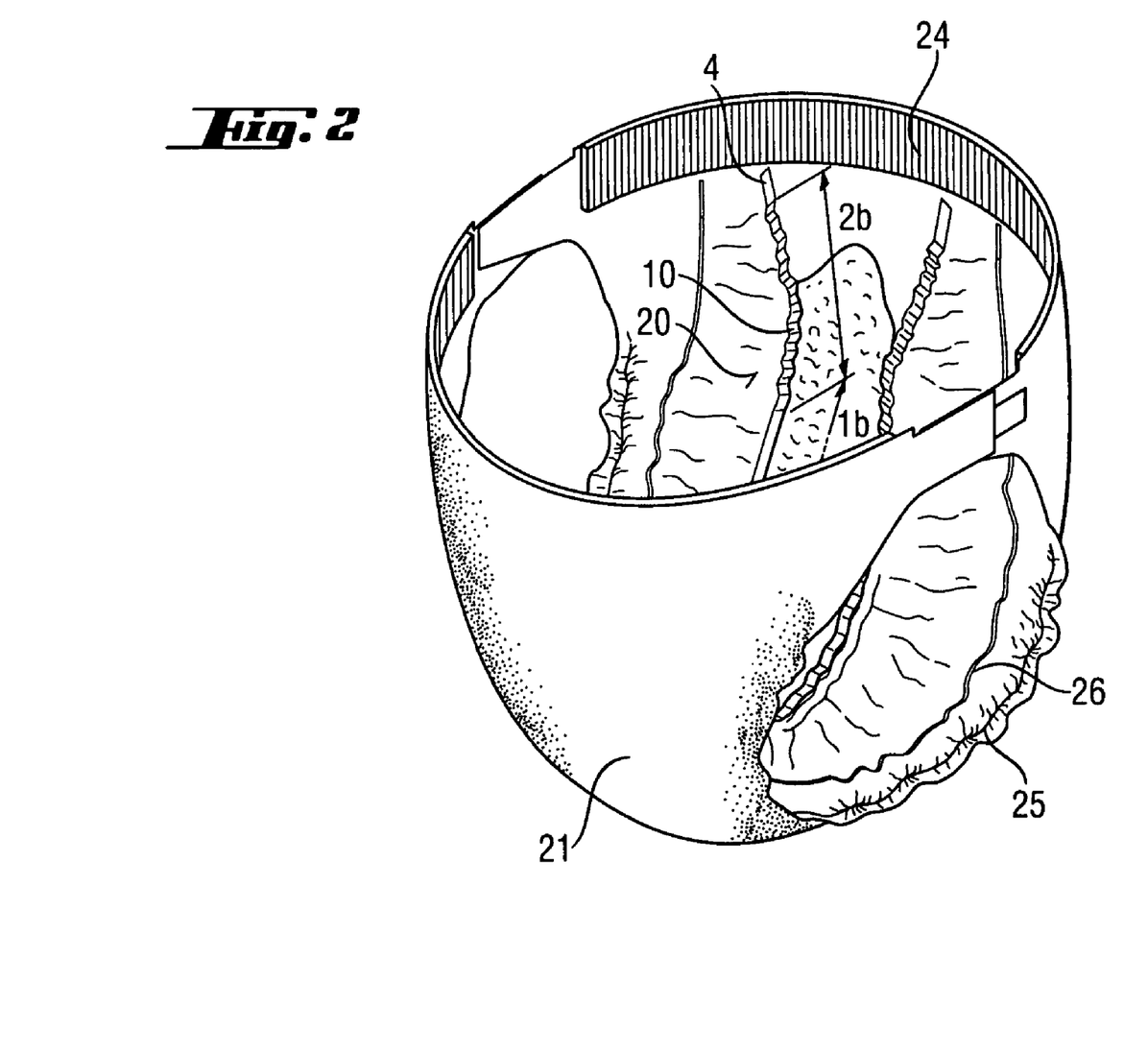
FIG. 2 shows a diaper in use, whereby the second zone (2b) is in a partially stretched state.
Figure 3:
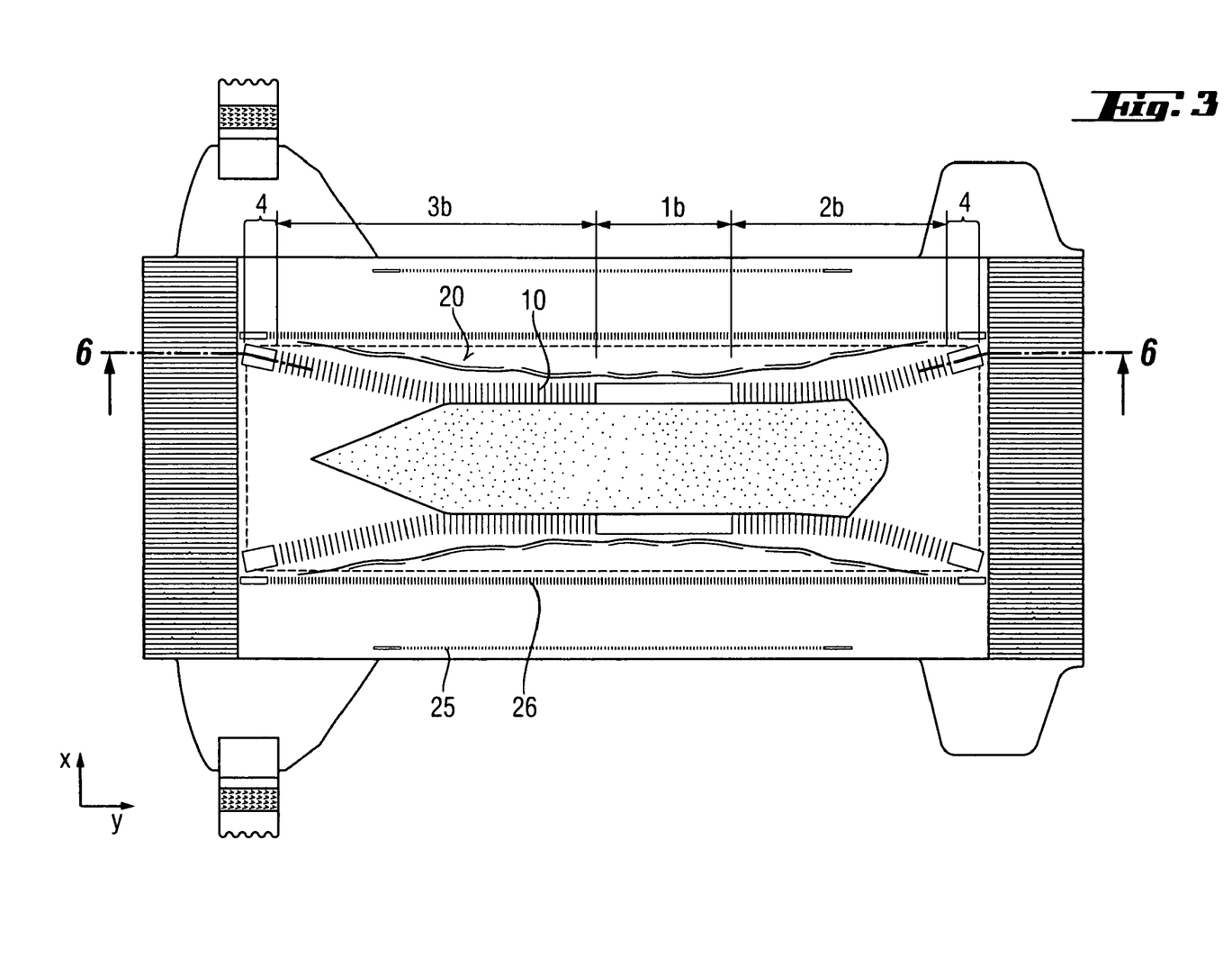
FIG. 3 shows a top view of a diaper in partially stretched state, whereby the first zone (1b) is only very slightly elongated in comparison to FIG. 1 and it has no wrinkles.
Figure 4:
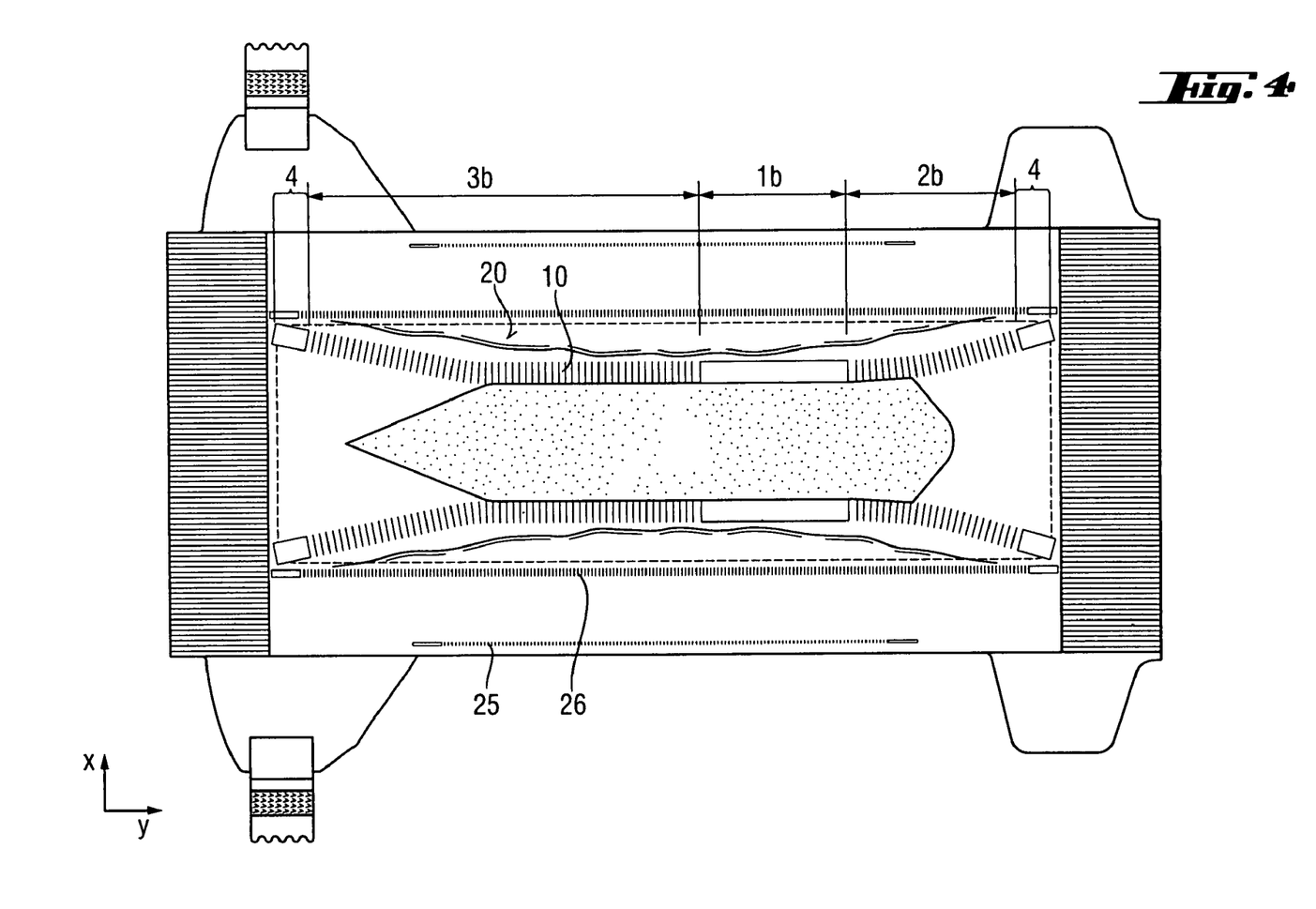
FIG. 4 shows a top-view of an alternative diaper, whereby the first zone (1b) is located slightly further towards the front waist region of the diaper, closer to where the genitals of a boy would be in use.

A suitable disposable absorbent article for use with present invention is a diaper, as shown in the FIGS. 1 to 5, that comprises a liquid pervious core coversheet or topsheet (20), a liquid impervious backsheet (21), an absorbent core— which may be positioned between at least a portion of the core coversheet, and the backsheet (21)—, elastic side panels (27), elastic leg cuffs (25), elastic barrier cuffs (26), elastic waist feature (24), and a fastening system (28). The article as shown in FIGS. 1, 2 and 3 has a first waist region, a second waist region, opposed to the first waist region and a crotch region located between the first waist region and the second waist region, each being about ⅓ of the length of the article.

In some embodiments, the backsheet (21) may be impervious to liquids (e.g., urine) and may comprise a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the article while still preventing exudates from passing through the backsheet. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996.

The different parts or components of the article may be attached to one another by any means known in thee art. For example, the attachment means may include a uniform continuous layer of adhesive, a patterned layer of adhesive, or an array of separate lines, spirals, or spots of adhesive. A suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Adhesives which have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The core coversheet or topsheet (20) may be compliant, soft-feeling and non-irritating to the wearer's skin. Further, at least a portion of the core cover sheet may be liquid pervious, permitting liquids to be absorbed by the absorbent core underneath. A suitable core cover sheet may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the core cover sheet includes fibers, the fibers may be spunbond, carded, wet-laid, meltblown, hydroentangled or otherwise processed as is known in the art.

A portion of the core coversheet may be made of a hydrophobic material or is treated to be hydrophobic in order to isolate the wearer's skin from liquids contained in the absorbent core, but then, at least a portion of the upper surface of the core coversheet is treated to be hydrophilic so that liquids will transfer through the sheet more rapidly, for example, by treating it with a surfactant or by incorporating a surfactant into the core coversheet. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating a surfactant in the core coversheet can be found in U.S. Statutory Invention Registration No. H1670 published on Jul. 1, 1997 in the names of Aziz et al.

Alternatively, the core coversheet may include an apertured web or film which is hydrophobic. This may be accomplished by eliminating the hydrophilizing treatment step from the production process and/or applying a hydrophobic treatment to the core coversheet, such as a polytetraflouroethylene compound like SCOTCHGUARD or a hydrophobic lotion composition, as described below. In such embodiments, the apertures may be large enough to allow the penetration of aqueous fluids like urine without significant resistance.

Any portion of the cuffs (26) or the core coversheet or the topsheet (20) described herein may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" issued to Roe on Mar. 4, 1997. The lotion may function alone or in combination with another agent as the hydrophobizing treatment described above. The core coversheet and/topsheet (20) may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson.

The absorbent core may comprise any absorbent material which is generally compressible, conformable, non-irritating to the wearer's skin, and capable of absorbing and retaining liquids such as urine and other certain body exudates. The absorbent core may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles, such as comminuted wood pulp, which is generally referred to as airfelt, and superabsorbent polymers or absorbent gelling materials; or any other known absorbent material or combinations of materials.

The article may also include a fastening system (28) that maintains the first waist region and the second waist region in a configuration so as to provide lateral tensions about the circumference of the article to hold it on the wearer. The fastening system (28) may comprise a surface fastener such as tape tabs, hook and loop fastening components and/or hermaphroditic fastening components; although any other known fastening means are generally acceptable. In alternative embodiments, opposing sides of the article may be seamed or welded to form a pant. This allows the article to be used as a pull-on type diaper or training pant. The term "training pants", as used herein, refers to disposable garments having fixed sides and leg openings designed for infant or adults wearers. Training pants (also referred in the art as "pull-on" products) are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993, U.S. Pat. No. 5,569,234, issued to Buell et al. on Oct. 29, 1996, U.S. Pat. No. 6,120,487, issued to Ashton on Sep. 19, 2000, U.S. Pat. No. 6,120,489, issued to Johnson et al. On Sep. 19, 2000, U.S. Pat. No. 4,940,464, issued to Van Gompel et al. on Jul. 10, 1990 and U.S. Pat. No. 5,092,861, issued to Nomura et al. on Mar. 3, 1992.

The article may also comprise side panels (27) that are elastic or non-elastically extensible to provide a more comfortable and contouring fit by initially conformably fitting the article to the wearer and sustaining this fit throughout the time of wear well past when it has been loaded with exudates since the elasticized or extensible side panels allow the sides of the article to expand and contract. Said side panels (27) may be the component with the elastic laminate portion (10) as described herein.

The article may include barrier cuffs (26) and/or leg cuffs (25) which provide improved containment of liquids and other body exudates. Said leg cuffs and/or barrier cuffs may each be the component(s) with the elastic laminate portion (10) as described herein below.

Component with the Elastic Laminate Portion(s) (10)

The component comprising or consisting (being or partially being) of the elastic laminate portion (10) herein has an x-direction, y-direction and z-direction and said laminate portion (10), and the component, has elastic stretch or elongation in a first direction, e.g., y-direction. For conciseness, the dimension of the component in the y-direction is herein referred to as "length" and the dimension perpendicular thereto and in the plane of the component is referred to as the x-direction and width, and the dimension perpendicular to the length and the width is referred to as z-direction and the height, caliper or thickness. However, the "length" does not have to be the longest dimension of the component; it is merely the dimension of the component in the average direction of stretch. For example, a component herein that is a waistband, leg cuff, barrier cuff, the y-direction and thus the direction the force is applied to obtain the elastic elongation or stretch, is typically also the longest dimension of the component, but, for example, for a component herein that is an elastic side panel, the y-direction is the direction of stretch or elongation, but the longest dimension may be in the x-direction.

The elastic laminate portion (10) has at least a first zone (1c) and a second zone (2c) that each has a different maximum elongation, as defined herein below, and/or that have a different wrinkle density and/or different wrinkle height, as defined herein. Each such zone is at least 2 cm, as can be understood from the test method below, for obtaining the stretched lengths and elongations of said zones.

Such zones may be obtainable by attaching to a supporting sheet one or more zones of an elastic material with a larger degree elongation than one or more other zone(s) of said elastic material.

Figure 15:
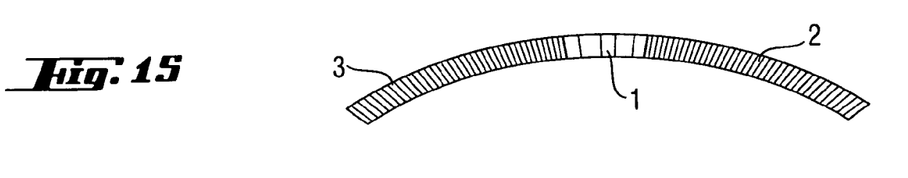
FIG. 15 shows a top-view of a curved laminate portion (10) in a contracted state.

The elastic laminate portion (10) may be straight, curved, as shown in FIG. 15, or it may comprise several straight parts that are joined under an angle with one another, as can been seen in FIGS. 1 to 5 and 13, or a combination of such configurations. This is herein referred to, respectively, as "straight", "curved" or "angled" elastic laminate portion (10) s, respectively, or, for example, "curved and angled" elastic laminate portion (10), etc.

The elastic laminate portion (10) has an absolute contracted length $L_c$, which is determined as follows:

The component with the elastic laminate portion (10) is removed from the absorbent article, such that the elastic profile is not changed.

The component is placed as flat as possible on a surface, without applying any elongating force to it. Then the absolute contracted length of the elastic laminate portion (10) of the component is measured. This is herein referred to as the absolute contracted length of the laminate $L_c$.

The laminate portion (10) has a fully stretched absolute length $L_s$, and the laminate portion (10) has zones (1c, 2c) of different elongation, as defined herein, which can be detected by the method below and furthermore, each zone (1c, 2c) thereof has a contracted absolute length $L_{czone\ 1,\ldots,x}$, and also a fully stretched absolute length $L_s$, $L_{szone1\ldots x}$, which can be determined by the method described below and in the "Method" section, namely as follows:

1) When the Elastic Laminate Portion (10) is Straight:

2 cm long sections are marked on the laminate portion (10) (in contracted, e.g., relaxed state, as set out above), with a very fine marker pen, resulting in a multitude of 2 cm long sections along the y-axis and possibly one section of less than 2 cm.

Then, the whole laminate portion (10) is elongated as set out in the method below, so that the maximum or fully stretched length is obtained and then, this absolute fully stretched length can then be measured, which is herein referred to as $L_s$. The maximum elongation can then also be determined by:

$$\epsilon = (L_s - L_c)/L_c.$$

Equally, the length of each section above that has been submitted to the method above and that may now elongated is measured.

The elongation of each section can be determined, as above, e.g.:

$$\epsilon_{section1} = (Ls_{section1} - 2\ cm)/2\ cm.$$

As defined herein, the laminate portion (10) has at least one section, herein referred to as first zone (1) that has an elongation of less than 50% of $\epsilon$. Typically, it has at least 2 consecutive sections that have an elongation of less than 50% of $\epsilon$, which together form the first zone (1).

Subsequently, the zones can be located and the contracted length $L_{czone1}$ can be determined (for example: 2 cm or 2×2 cm) and the fully stretched absolute length of such first zone $L_{szone1}$ can be determined (for example: 2.5 cm, or 2×2.2. cm=4.4 cm), and the elongation of the first zone $\epsilon_{zone1}$ can be calculated as above.

A section that has an elongation of more than $\epsilon$ is herein referred to as a second zone (2c), and if there are consecutive sections with an elongation of more than $\epsilon$, then they form together a second zone (2c). For such a second zone (2c), the $L_{czone\ 2}$ can be determined (e.g., 2 cm or 2×2 cm, or 2×2 cm), and as above, the fully stretched absolute length of such second zone (2c) $L_{szone1}$ can be determined (for example: 4 cm, or 2×3.6. cm=7.2 cm), and the elongation of the first zone (1c) $\epsilon_{zone1}$, as above.

Sections with an elongation of more than $\epsilon$ that are positioned on different sides (in y-direction) of the first zone (10) are herein referred to as different zones, e.g., second and third zone (2c, 3c).

Figure 13:
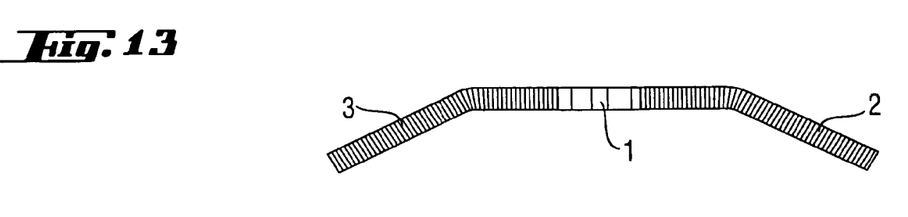
FIG. 13 shows a top-view of an angled laminate portion (10) in contracted state.

2) When the Elastic Laminate Portion (10) is "Angled":

The laminate portion is divided by marking with a fine marker pen into straight parts (i.e., between the angles), for example, in 3 straight parts, as can be seen in FIGS. 3 and 13.

The contracted absolute length $L_c$ is obtained by adding up the contracted lengths of the straight parts of the laminate portion (10) (e.g., if it comprises 3 straight parts that are connected to one another with two angles, then the contracted absolute length of the 3 portions (10) are measured and added up.)

Then, each straight part is divided by a fine marker pen into sections of 2 cm length, and possible a section of less than 2 cm. Subsequently, each straight part is elongated. The fully stretched absolute length of the laminate portion $L_s$ is obtained by adding up the fully stretched lengths of the straight parts of laminate portion (10). The elongation and stretched length of each section (e.g., of original contracted length of 2 cm) in each straight part are determined, and subsequently the first zone (1c) and second zone (2c) and optionally further zones (3c, ...) are located and the lengths and elongations thereof can be determined, following the method as set out above with respect to a straight laminate portion (10).

3) When the Elastic Laminate Portion (10) is Curved:

The curved elastic laminate portion (10) is divided with a fine marker pen into sections of 2 cm absolute length and possibly one remaining section of a smaller length.

Each section has two transverse edge lines that are 2 cm apart, and each transverse edge line has a centre point. A line can be drawn through said two points of said two transverse edge lines. This will be the "y-direction line" along which the force will be applied in the method below, to elongate said section. This will be done for each section. Thus, the fully stretched length of each section and the elongation thereof can be determined.

After stretching all sections, a fully stretched absolute length of each section is measured. Then, the absolute stretched length of the laminate portion can be calculated by adding up these values for the different sections.

The first and second zone (1c, 2c) can then be located as set out above, and their fully stretched lengths and elongation can be determined as set out above.

4) Mixed Elastic Laminate Portions

If the elastic laminate portion (10) comprises a combination of curved, angled and/or straight parts, then a combination of the above methods is applied accordingly.

The elastic laminate portion (10) has an (e.g., substantially y-direction) elongation $\epsilon$ (maximum) of at least 0.6, at least 0.8 at least 1.0 at least 1.2, or it may be at least 1.4.

Figure 7:
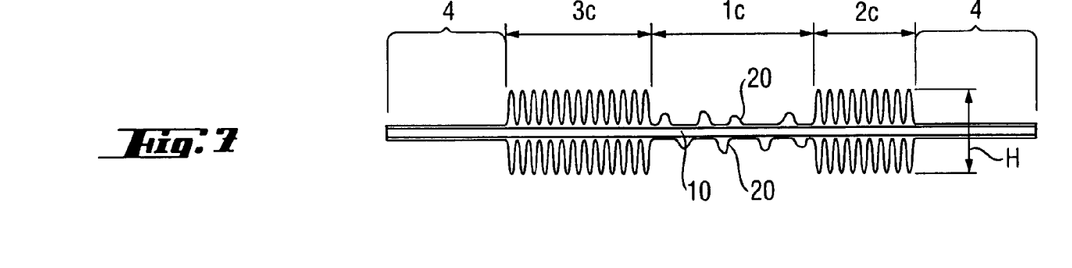
FIG. 7 shows a cross-sectional side-view of the laminate portion (10) in a contracted state.
Figure 8:
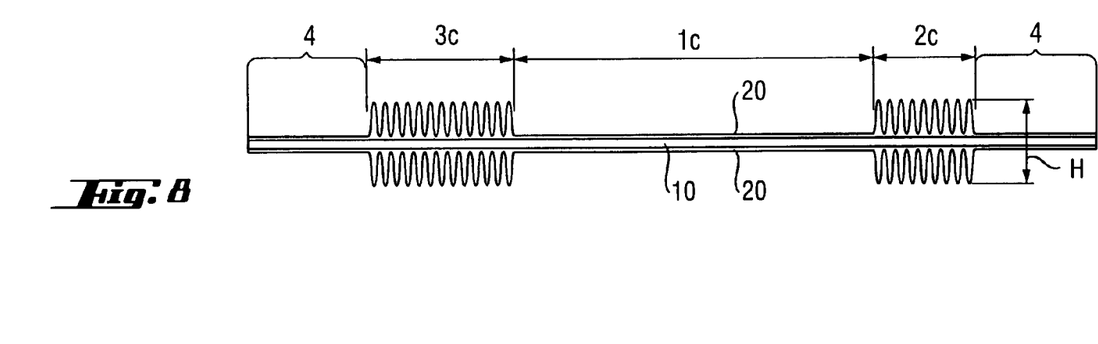
FIG. 8 shows a cross-sectional side-view of an alternative laminate portion in contracted state whereby the first zone (1c) does not comprise any wrinkles and has no elongation potential.
Figure 9:
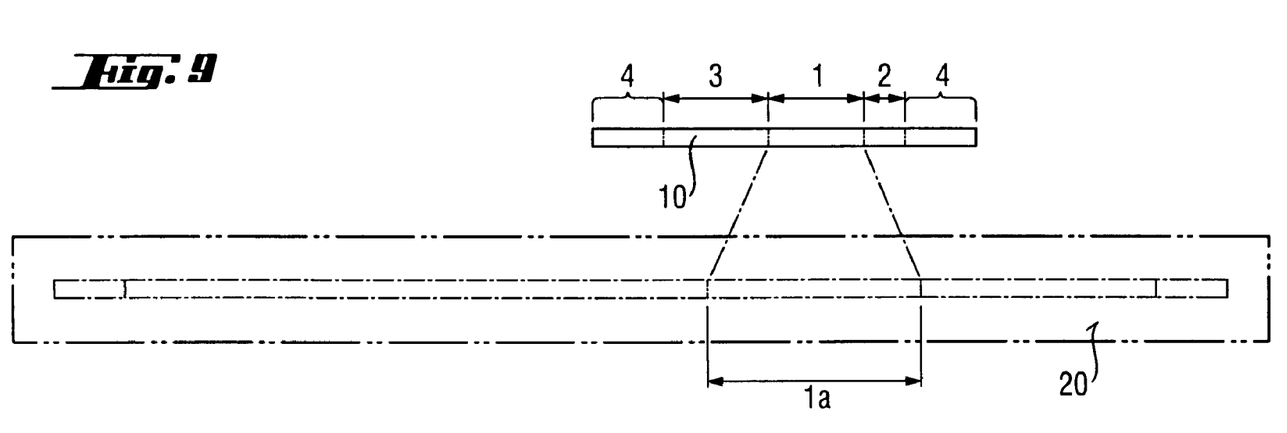
FIGS. 9 to 11 show a schematic top-view of how the elastic laminate portions (10) may be obtained.
Figure 10:
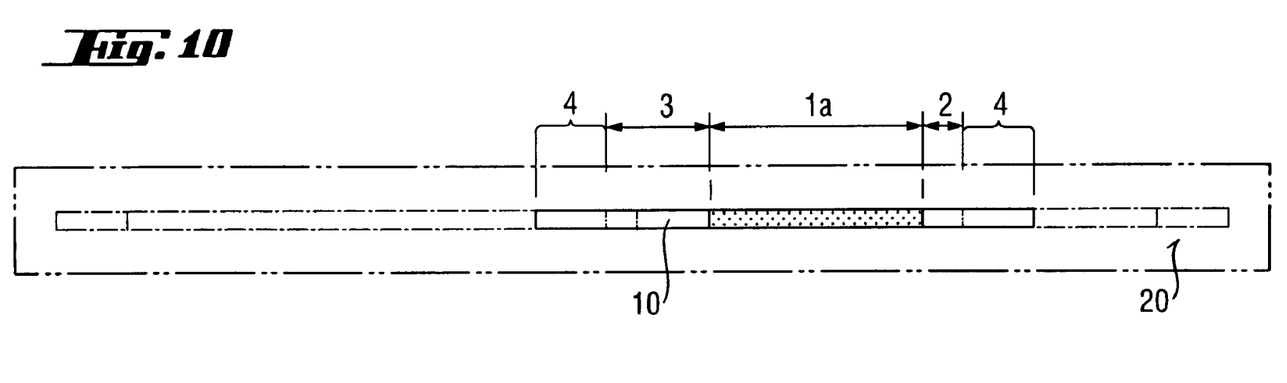
Figure 11:
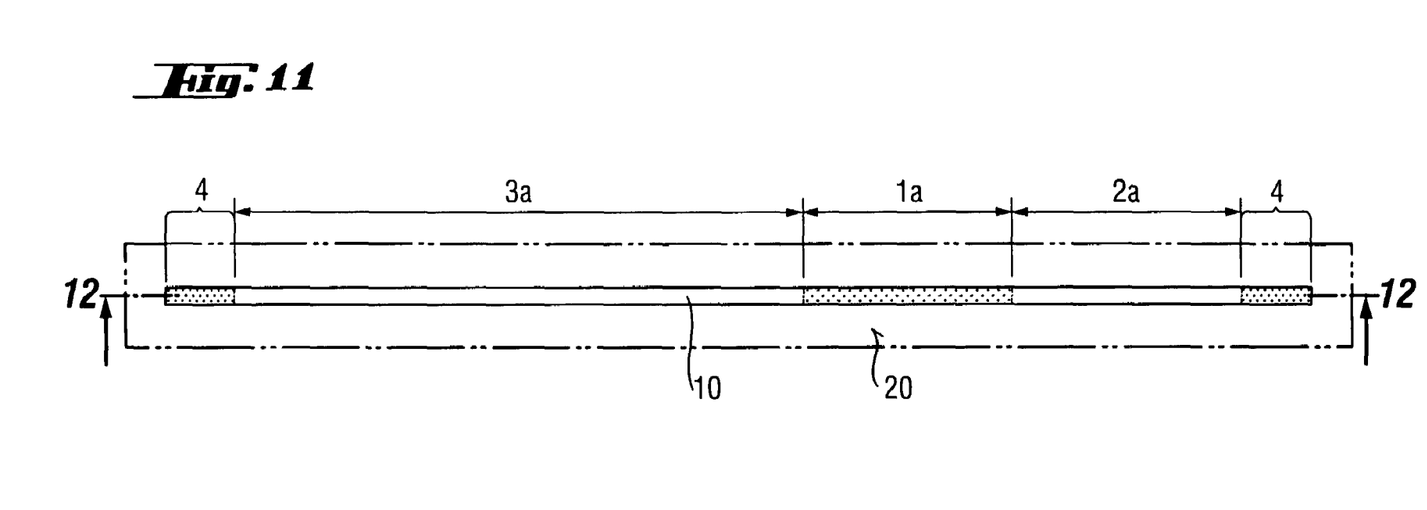
Figure 12:
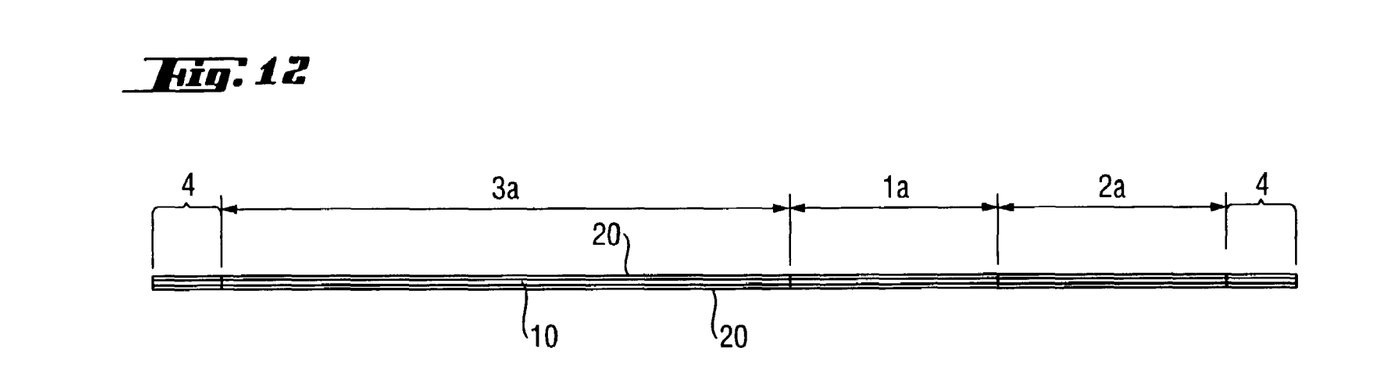
FIG. 12 shows a cross sectional side view of the resulting laminate (10).

The elastic laminate portion (10) has as least two zones (1b, 2b), a first zone (1b) and a second zone (2b) and, optionally, further zones (third zone (3b), fourth zone etc.) in the y-direction, with a different degree of maximum elongation potential in this y-direction, and/or a different wrinkle height and/or a different wrinkle density, each being at least 2 cm in contracted (relaxed) state, as can be seen from FIGS. 7-8.

The elastic laminate portion (10) may comprise at one or both longitudinal ends an attachment portion (4) where the elastic is attached to the supporting sheet and where there may not be any wrinkles, and that has an elongation of less than 0.2, or even 0. These attachment areas are typically very small, having a length of less than 2 cm, or typically less than 1.5 cm or even less than 1 cm, or even less than 0.5 cm. However, in another embodiment herein, the elastic laminate portion is attached to the supporting sheet such that no such attachment portions (4) are formed on either longitudinal end thereof.

In a first embodiment, each zone (1b, 2b) has fully stretched absolute length ($L_{szone1}$, $L_{szone2}$, $L_{szone3}$, etc.) and a contracted absolute length ($L_{czone1}$, $L_{czone2}$, $L_{czone3}$ etc.) and a maximum elongation ($\epsilon_{zone1}$, $\epsilon_{zone2}$, $\epsilon_{zone3}$, etc.), determined as follows: $\epsilon_{zone1}=(L_{szone1}-L_{czone1})/L_{czone1}$ and so forth for each zone (1b, 2b), whereby said values are obtained as set out above.

In a first embodiment, the first zone (1b) has a maximum elongation $\epsilon_{zone1}$ which is much less than the average elongation $\epsilon$ of the whole elastic laminate portion (10) and consequently, the second zone (2b) at least has a maximum elongation $\epsilon_{zone2}$, which is more than the average elongation $\epsilon$ of the elastic laminate portion (10) as a whole. This is further shown in the Figures.

Herein, the first zones 1a, 1b and 1c are as follows: first zone (1c) in the elastic laminate portion (10) shows the contracted state; first zone (1b) in the elastic laminate portion (10) shows the partially stretched state; the elastic material is shown as first zone (1a). The same applies to the second and third zones (2a, 2b, 2c) and (3a, 3b, 3c).

Typically, $\epsilon_{zone1}$ is less than 50% of $\epsilon$, even less than 40% of $\epsilon$, or even less than 30% of $\epsilon$, or even less than 20% of $\epsilon$, or in another embodiment the first zone (1c) may have no elongation potential and $\epsilon_{zone1}$ is 0. The latter can be seen in FIGS. 5 and 8, where the first zone (1c) has no wrinkles in contracted state (1c), and has no elongation potential.

The elastic laminate portion (10) herein has at least in contracted state and in partially stretched state (elongation=0.5) wrinkles formed from the supporting sheet material(s).

In the first zone (1c), the average wrinkle height of the wrinkles may be less than the average wrinkle height of the wrinkles in the second (and optionally or preferably third) zone (2c, 3c), and less than the average wrinkle height of the elastic laminate portion (10) as a whole (on average).

In one embodiment of the invention the absorbent article comprises a component with an elastic laminate portion (10) that has, at an elongation $\epsilon=0.5$ (as determined by the method described herein), an average wrinkle height ($H_w$) and the first zone (1b) has in this embodiment an average wrinkle height $H_{wzone1}$ of less than 50% of $H_w$, less than 30% or even less than 20% of $H_w$ or even less than 10% $H_w$, or the first zone (1b) has even no wrinkles at all ($H_{wzone\ 1}$ is about 0).

The second zone (2b) has typically an average wrinkle height $H_{wzone2}$ of at least 1.1 $H_w$, or at least 1.2 $H_w$, or at least 1.3 $H_w$ or at least 1.35$H_w$.

$H_w$ may, for example, be between 600 microns and 1000 microns, or, for example, to 850 micron and $H_{wzone1}$ may be 300 microns or less, 200 microns or less, or even about 0. $H_{wzone2}$ may be from 700 to 1200 microns, or from 750 to 1000 microns.

In another embodiment, or in addition, the average wrinkles density (amount of wrinkles per cm lengthwise) is less in the first zone (1b) than in the second zone (2b) (and than in, for example, the third (3b)) zone) and less than the average wrinkle density of the elastic laminate portion (10) as a whole.

At an elongation $\epsilon$ of 0.5, the laminate portion (10) may have a wrinkle density $D_w$ (wrinkles per cm) and said first zone (1b) has, at an elongation $\epsilon$ of 0.5, a wrinkle density $D_{wzone1}$ of less than 50% of $D_w$, even less than 30% of $D_w$, or even less than 20% or even less than 10% of $D_w$, or even no wrinkles at all, i.e., a wrinkle density of about 0.

Typically, $D_w$ at this elongation of 0.5, is at least 7.5 wrinkles per cm. $D_{w1}$ may be 5 wrinkles per cm or less, or even 3 wrinkles per cm or less or even 0 wrinkles.

The second zone (2b) has an average wrinkle density of more than the average wrinkle density of the first zone (1b) and more than the average wrinkle density of the elastic laminate portion (10), being at least 1.1. $D_w$, or at least 1.2$D_w$, or even at least 1.25 $D_w$.

Figure 5:
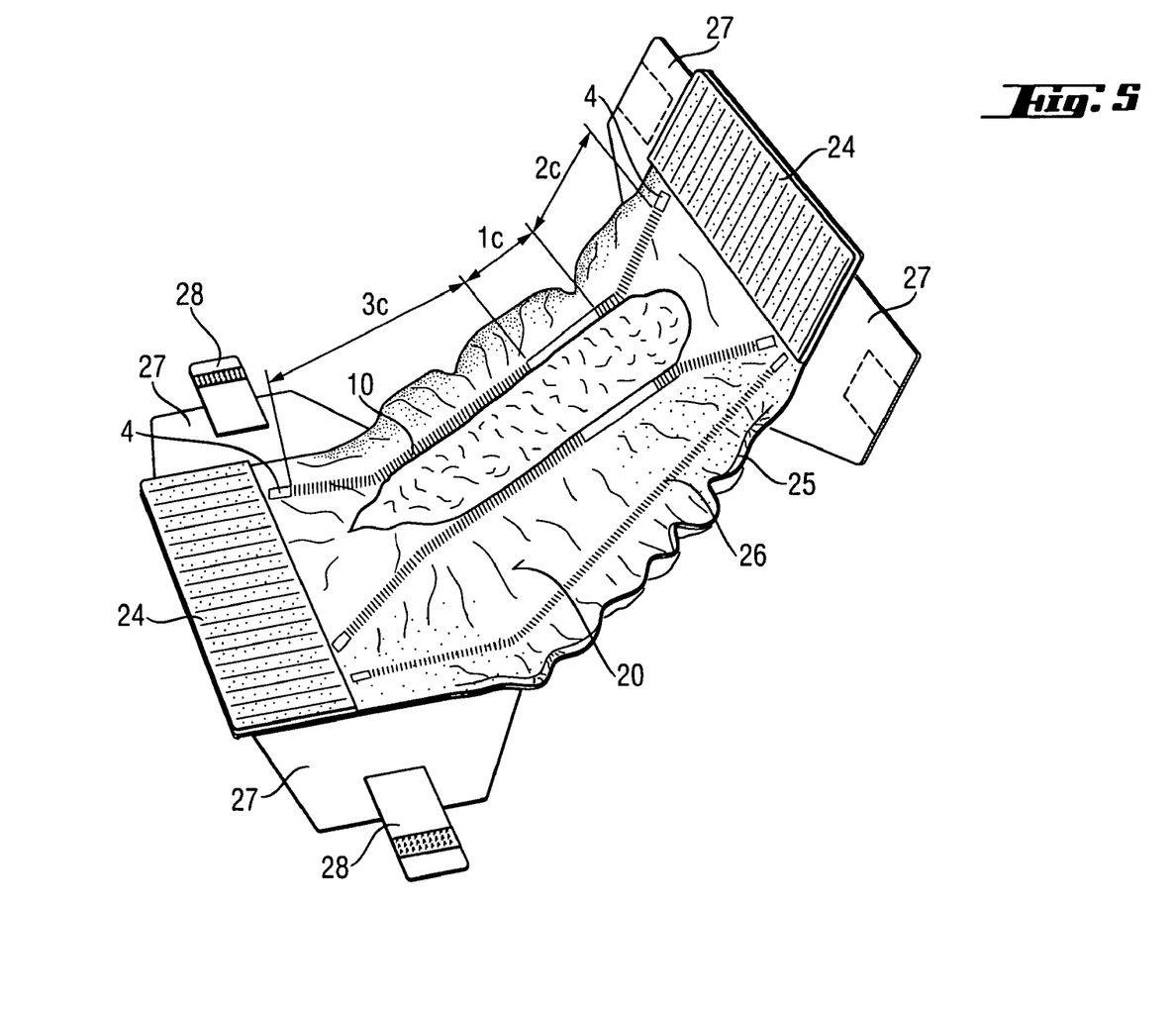
FIG. 5 shows a perspective view of an alternative diaper whereby the first zone (1c) comprises elastic material but does not comprise any wrinkles even in contracted state.
Figure 6:
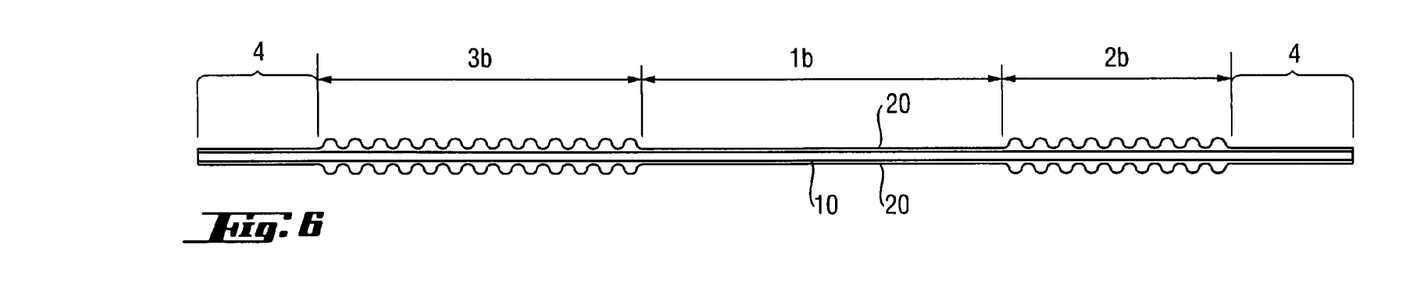
FIG. 6 shows a cross-sectional side-view of a laminate portion (10) in a partially stretched state.

In another embodiment, the first zone (1c) is in use positioned in contact with the skin area that is closest to the genitals, typically it may be positioned in the front 50% or even in the front 40% (length wise) of the article, as shown in FIG. 5 and possibly not in the front 10% or even not in the front 20% of the length of the article, as shown in FIG. 5, or, for example, in the crotch region of the article, as shown in FIG. 1. In another embodiment said first zone (1c) may, for example, be in closest proximity to the belly button.

The maximum elongation potential of the second zone (2c), $\epsilon_{zone2}$ is more than $\epsilon$, 110% $\epsilon$, or 120% $\epsilon$ or even 130% $\epsilon$.

The absolute contracted length of the first zone ($1c$) ($L_{czone\ 1}$) is at least 2 cm, or it may be more, e.g., 2×2 cm, or 3×2 cm.

$L_{czone\ 1}$ may be at least 20% or at least 30% of $L_c$, but typically at the most 60% $L_c$ or at the most 50%.

The second zone ($2c$) may have the same length in contracted state $L_{czone2}$ as the first zone ($1c$) above, or it may have a larger length than the first zone. It may be positioned in the back (length wise) 50% of the article, or, for example, in the back waist region.

The elastic laminate portion (10) may also comprise further zones, e.g., a third zone ($3c$) with a maximum elongation $\epsilon_{zone3}$ of more than the maximum elongation of the first zone ($1c$) $\epsilon_{zone1}$, and typically more than the average maximum elongation $\epsilon$ of the whole elastic laminate portion (10), and this may be equal to the maximum elongation of the second zone ($2c$) $\epsilon_{zone2}$. It has a $L_{czone3}$ of at least 2 cm.

The first zone ($1c$) is typically positioned between the second ($2c$) and third zone ($3c$) (in the y-direction orientation). For example, if the second zone ($2c$) is located in the back 40% or 50% (lengthwise) of the article or component, then the third zone ($3c$) may be positioned in the front 30% or 20% (lengthwise) of the article or component, e.g., in part of the front waist region, with the first zone ($1c$) therein between. Attachment portions (4) may or may not be present on both longitudinal ends of the elastic laminate portion (10).

Typically the third zone ($3c$) has an average wrinkle height $H_{wzone3}$ that is more than the average wrinkle height of the first zone $H_{zone1}$, and typically that is more than $H_w$, for example, being the same as $H_{wzone2}$.

The third zone ($3c$) has then an average wrinkle density $D_{wzone3}$ that is more than the average wrinkle density of the first zone $D_{wzone1}$; it may have an average wrinkle density $D_{wzone3}$ of about the same as the average wrinkle density of the elastic laminate portion (10) $D_w$ as a whole, but typically the third zone ($3c$) has an average wrinkle density that is more than said average $D_w$ and, for example, the same as (or more than) the average wrinkle density of the second zone $D_{wzone2}$.

The wrinkle densities and wrinkle heights can be determined by the Primos method described below.

Visualization of a transverse edge, i.e., a boundary, of a zone may also be done by use of the Primos method, as known in the art, and described below, by visualizing the line where either:

the height of the wrinkles on one side, (along 2 cm length), is smaller than the height of the wrinkles on the other side of said line, (along 2 cm length), or the line where on one side no wrinkles are present and on the other side wrinkles of a certain height are present (each along 2 cm length); or the density of the wrinkles on one side (along 2 cm length) is less than the density of the wrinkles on the other side of said line (along 2 cm length), or the line where on one side no wrinkles are present and on the other side wrinkles are presenting a certain density (each along 2 cm length).

The supporting sheet(s) may be any material compatible with the lamination to an elastic material (12). The supporting sheet is typically not itself elastically stretchable in the y-direction. The supporting sheet herein may even be relatively stiff material. In one embodiment, the component, or the part of the supporting sheet that is to form the elastic laminate portion (10), has a bending stiffness of at least 4 μNm, or even at least 8 μNm, or even at least 10 μNm or even at least 12 μNm. It may be a material with a relative high basis weight, namely at least of 10 gram per m² or even at least 15 gram per m², or even at least 20 gram per m² or even at least 25 gram per m². This may be determined by use of a KES-FB2 (pure bending) tester, available from Kato Tech Co Ltd, Japan, following the operating procedures of this equipment.

Supporting sheets suitable for use with the present invention include, but are not limited to woven and non-woven materials of natural fibers (e.g., wood or cotton fibers) and/or synthetic fibers. Some nonlimiting examples of thermoplastic fibers for use with the supporting sheet of the present invention include: polyolefins, polyesters, polyurethanes, and polyamides.

The fibers may be spun bond, carded, wet-laid, melt blown, and/or hydro entangled, and/or otherwise processed as is known in the art. The supporting sheet may comprise a non-woven material that comprises at least meltblown fibers; the meltblown fibers having a basis weight in said material of at least 5 gram per m², or even at least 7 gram per m², or even at least 10 gram per m² or even 15 grams per m² (the maximum amount being limited by the basis weight of the supporting sheet as a whole, as defined above).

The supporting sheet may be air permeable. In certain executions herein, e.g., leg cuffs (25), barrier cuffs (26), it may be preferably that it has high barrier properties.

The supporting sheet may have micro pores that have a uniform pore size distribution. The supporting sheet may have pores with a maximum pore size (bubble point diameter) of less than 100 μm, less than 75 μm, less than 50 μm and less than 25 μm. The pores may have a mean pore size of less than 20 μm, less than 17 μm, less than 13 μm or less than 10 μm.

It may be preferred that the supporting sheet is a portion (10) of two or more sheets or webs. For example, it may comprise at least two layers, one of which is a meltblown (M) layer and another is either a spunbond (S) or a carded (C) layer.

Suitable executions are SM SMS, SMMS, SSMS, SSMSS, SSMMS, CM or CMC non-wovens laminates. It may be preferred that one surface, web or layer of the supporting sheet is treated with a surface energy reducing agent described herein.

Said non-woven webs may be formed from polyethylene, polypropylene and/or polybutylene polymer fibers, or (a mixture of) fibers of a copolymers of polyethylene, polypropylene and/or polybutylene.

Examples of materials used as supporting sheets include 34 gsm SMS polypropylene non-woven laminates having a maximum pore size (pore size) of 32 μm, an airpermeability of 34 Darcy/mm, available from Pegas under the name Pegaphob 02 445 032; a 24 gsm SSMMS polypropylene non-woven laminates, having a maximum pore size of 57 μm, for example, available from Pegas under the name Pegaphob 02 445 024; a 34 gsm SSMMS polypropylene non-woven laminates, having a maximum pore size of 48 μm, for example, available from Pegas under the name Pegaphob 02 445 032; a 20 gsm web available from Sandler under the code VP21/00/75, having a maximum pore size of 22 μm; or a 20 gsm web available from Sandler under the code VP21/00/76, having a maximum pore size of 23 μm. Such materials may, for example, be treated with Dipolit, to reduce the surface energy of the materials.

It may also be preferred that the supporting sheet comprise ingredients, which reduce friction between the wearer's skin and the supporting sheet, or in particular between the skin and the elastic laminate portion (10). Hereto, the component, e.g., the laminate portion (10) or supporting sheet, may, for example, comprise a lotion, a fine powder, such as talcum powder or wax.

The component, supporting sheet or laminate portion (10) may be treated with an agent to reduce its surface energy. For example, useful agent include fluorocarbons as described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000. Other agents include silicone. Useful methods for applying the agent to the material, without reducing the air permeability, can be found in U.S. Pat. No. 5,322,729 and PCT Publication WO 96/03501. Nonlimiting examples of agents suitable for use with the present invention include fluorocarbons, siloxanes, polysiloxanes, including fluorinated monomers and fluorinated polymers, including hexafluoroethylene, hexafluoropropylene and vinyl fluoride and vinylidene fluoride, fluoroacrylate and fluoromethacrylate. The component may be provided with poly(tetra) fluoroethylene, fluorinated ethylene-propylene copolymers and/or fluorinated ethylene-tetrafluoroethylene copolymers.

In another embodiment the component with the elastic laminate portion (10) herein is a barrier cuff and/or leg cuff of a diaper, training pants or adult incontinence product.

In these instances, the supporting sheet may be hydrophobic and/or urine-impermeable.

The articles of the present invention comprise at least one elastic laminate portion (10). The elastic laminate portion may be either two separate components or one component, as described herein, namely as a pair of leg cuffs (25) and/or barrier cuffs (26) that extend in longitudinal direction along the longitudinal edges of the diaper, as known in the art.

The elastic material (12) may extend over the whole length and width of the support sheet, but it may be preferred that said elastic material(s) (12) do(es) not extend over the whole width of the support sheet, at least.

In another embodiment, an elastic laminate portion (10) is formed by attaching one or more strands or bands of elastic material (12) to a support sheet; such a laminate portion (10) is considered a single laminate portion (10) if it operates in use as such, e.g., if the elastic strands or bands are attached to the supporting sheet in the same manner (e.g., parallel) and so close together that in use a laminate portion (10) is obtained that acts as a unitary elastic portion (10). Typically, the average distance between the elastic bands or stands in a unitary elastic laminate portion (10) is 1-5 mm, or 1-3 mm.

The width of the elastic laminate portions (10) will vary, typically depending on the exact dimensions of the component, e.g., waist band (24) and/or leg cuff (25) of the article.

For example, when the elastic laminate portion (10) is part of a leg cuff (25) or barrier cuff (26) may have an average width of less than 3 mm, e.g., about 0.2 to 3 mm, or even from 0.3 to 1.5 mm.

The elastic laminate portion (10) herein that is part of a waist band (24) may have an average width of 1 cm to 6 cm, or from 1.5 to 4 cm and the side panel comprising or consisting of the elastic laminate portion (10) herein may, for example, have an average width of 2 cm to 15 cm, or even 3 to 10 cm.

Also, the length of the elastic laminate portion (10) will typically depend on the size of the component or the article. For example, for a size 4 diaper the laminate portion (10) of a component that is a leg cuff (25) or barrier cuff (26) herein may be in fully stretched state on average at least 25 cm, or from 35 cm to 45 cm.

Any elastic material (12) may be used for the purpose of the present invention. Some nonlimiting examples include VFE-CD, available from Tredegar, L-86, available from Fulflex (Limerick, Ireland) or L-89, available from Fulflex.

The elastic materials (12) used herein typically have a thickness (e.g., gauge) of at least 20 microns, at least 40 microns, or even at least 60 microns, typically up to about 300 microns, or even up to 200 microns or even up to 150 microns. Some suitable elastic materials have a thickness of about 70 to 100 microns.

The inventors found that by introducing one or more zones ($1b$, $2b$) of reduced maximum elongation, or no elongation at all, and having typically smaller wrinkles and/or wrinkle densities, reduced pressure marks are obtained. However, the overall elastic profile of the components with the elastic laminate portions (10) and of the article can be maintained. Thus, the component with the elastic laminate portion (10) and/or the laminate portion (10) herein is such that it typically has the following elastic profile, despite the first zone ($1b$) of reduced elongation; either:

a) 1.5 Lt by a first load force of less than 1.1N or even less than 0.6N, 3.0 Lt by a first load force of less than 2.1N or even 1.1N and 4.5 Lt by a first load force of less than 3.0N or even less than 1.5N and a second unload force at 4.5 Lt of more than 0.9N, a second unload force at 3.0 Lt of more than 0.5N and a second unload force at 1.5 Lt of more than 0.1N.

(Said elastic profile obtainable by the method set out in co-pending application EP1201212-A, whereby Lt is the contracted length of the component, herein referred to as $L_c$).

or:

b) 0.25 $L_s$ by a first load force of less than 0.6 N, 0.55 $L_s$ by a first load force of less than 5N or even less than 3.5 N and 0.8 $L_s$ by a first load force of less than 10.0N or even less than 7.0N and a second unload force at 0.55 $L_s$ of more than 0.4N, and a second unload force at 0.80 $L_s$ of more than 1.4N, or even more than 2.0N.

(Said elastic profile obtainable by the method set out in co-pending application EP1201212-A, whereby $L_s$ is as specified herein.)

The component or elastic laminate portion (10) may have a force profile such that it has a first load force at 200% elongation of 1.6 N or less, and a second unload force at 200% elongation of 0.5 N or more.

Process

The component or laminate portion (10) can be obtained by, for example, a process comprising the steps of:

a. obtaining a support sheet material that is such that it has its maximum length dimension;

b. obtaining an elastic material (12) and elongating at least one first part thereof, by an elongation of less than 0.3, or leaving at least said first part non-elongated, said part having an absolute contracted length $L_{czone1}$ (in y-direction) of at least 2 cm; and c. elongating at least a second part thereof such with an elongation of at least 0.7;

d. applying said first parts as obtained in step b. to the support sheet to form a first zone ($1a$), e. applying said second parts as obtained in step b. to the support sheet to form a second zone (2), to thus obtain an elastic laminate portion (10) with at least said first zone ($1a$) and said second zone (2) of different elongation.

Hereby, step d. may be applied prior to step c. Also, step d. and optionally step e. may be applied prior to step b.

This is further shown in FIGS. 9 to 12.

The elastic material (12) may be attached to the support sheet by any known method, including adhesive or heat bonding. They may be attached such that no attachment portions (4) are obtained that do not have any wrinkles, or such that only small attachment portions (4) are obtained, having a length (in direction of length of the elastic laminate portion (10)) of less than 1 cm, or even less than 0.5 mm.

Another method of attaching elastic bands or strands to a supporting sheet is described in co-pending European application 03022089.1, filed 1 Oct. 2003, because that may also reduce any pressure marks by the second and third or further zones with the higher elongation and elasticity.

Figure 14:
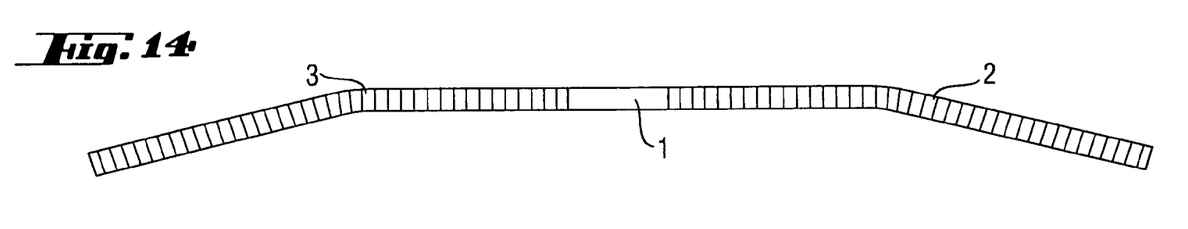
FIG. 14 shows the laminate portion of FIG. 13 at an average elongation of about 0.5.
Figure 16:
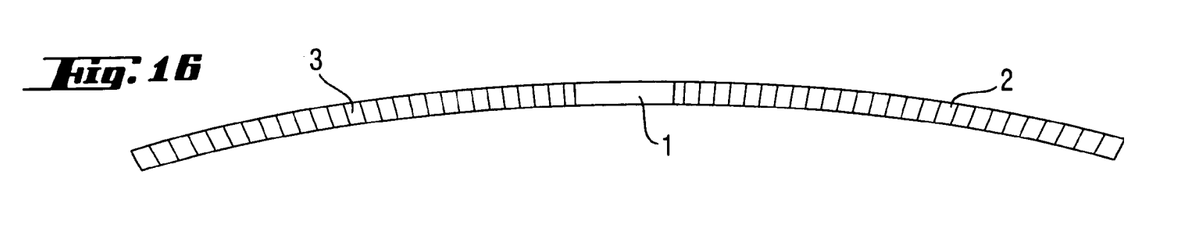
FIG. 16 shows this laminate portion of FIG. 15 at an average elongation of about 0.5.

Test Methods:

Method to Stretch to its Fully Stretched Length (in Order to Define and Determine (the Position of the) Zones, Ls and $L_{szone1,2,...x}$, and Elongations) or to an Elongation of $\epsilon$=0.5:

For the calculations set out above, either the laminate portion (10) as a whole (when straight), a straight part thereof (when comprising straight angled parts, as in FIGS. 13 and 14), or sections (when curved, as in FIGS. 15 and 16) thereof—hereinafter referred to as sample—will be stretched by applying a force thereto. This is done as follows.

The component (comprising said "sample(s)") or if possible the elastic laminate portion(s) (10) thereof (comprising said "sample(s)") are obtained by removing this from the absorbent article such that the elongation potential, wrinkle height and wrinkle density are not changed.

It is left for 24 hours at 25° C. and 50% humidity, prior to the elongation/stretching step below, which is subsequently performed under the same conditions.

Measurement of lengths of sections/samples can be done with a micrometer screw. (Each) sample to be tested is placed length-wise (in the direction of stretch) between two tweezers or, if the width of the sample is more than 1 cm, between two clamps of a width of 1 cm, one on each end, such that contact area of the tweezers/clamp and the sample is at the most 1 mm for clamps and 0.5 mm for tweezers in the direction of stretch (length). The exact distance between the start of one clamp or tweezers to the beginning of the other clamp or tweezers is measured. This is the contracted length of the sample, e.g., of the laminate portion, the straight part thereof or section thereof, i.e., 2 cm, as marked between the marker pen lines.

Then, the sample is stretched to its maximum elongation (e.g., when the support sheet reaches its maximum length and the length of the sample and the distance between the clamps is measured, and the elongation $\epsilon$ is calculated.

For straight samples, the clamps or tweezers are moved in the y-direction of the length of the straight samples, such that the length direction is the direction of the elongation force.

For curved samples, the clamps are moved along the force line as determined above.

Elongation of $\epsilon$=0.5:

The densities and wrinkle heights are measured on a elastic laminate portion (10) when it has an "elongation $\epsilon$ of 0.5", which means herein the following.

If the elastic laminate portion (10) is straight, the component and/or laminate portion (10) as a whole is elongated or stretched to the length that it has an elongation $\epsilon$=0.5 (e.g., if $L_c$ is 20 cm, the laminate portion (10) is stretched to $L_s$=30 cm,). This laminate portion can then be tested in the method below.

If the elastic laminate portion (10) has straight parts that are connected by angles, as described above and shown in the FIGS. 1 to 5 and 13 and 14, each straight section is elongated by an elongation of 0.5, or if this is not possible (e.g., if one straight section coincides with a first zone (1) with hardly any or no elongation potential, then it should be stretched to its maximum elongation (which should thus be less than 0.5). Then, this laminate portion can be tested in the method below.

If the elastic laminate portion (10) is curved, as described above and shown in FIGS. 15 and 16, each 2 cm section is elongated (by use of tweezers or clamps) to an elongation of 0.5, or if this is not possible, to its maximum elongation (which should be les than 0.5). Then, this laminate portion (10) can be tested in the method below.

In each case, the stretched elastic laminate portion (10) is fixed it this partially stretched position of $\epsilon$=0.5 by conventional means onto a testing surface (e.g., glue, pin) and then the tweezers used to stretch the elastic laminate portion are carefully removed, ensuring the position of the elastic laminate portion is not moved.

Defining the Zones of Different Wrinkle Height or Density, and Quantifying these Parameters The following described a method to visualize the boundaries of the zones (1, 2) herein, and/or a method to determine the wrinkle height and winkle density of the laminate portion (10) of the component, sections and zones thereof.

Each sample with the elongation of 0.5 as defined and obtained by the method above, is examined by use of PRIMOS and its data acquisition software, following the manufacture's instructions manual, using a 13×18 mm lens.

The PRIMOS equipment and software will calculate the average wrinkle height and density of the sample, e.g., of the laminate as a whole or a section thereof, or part thereof. Then, the first and second zones can be identified, following the method outlined above for the elongation of the zones. The average wrinkle height and density of each section and identified zone (e.g., one or more sections) can be calculated.

If the elastic laminate portion has an average width of more than 3 mm, then the measurement above is only done on the inner 70% of the width of the laminate portion, along its full length.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article, the disposable absorbent article comprising:
   a first waist region; a second waist region; and a pair of outermost longitudinal edges connecting the first waist region and the second waist region;
   a pair of elongate outer elastic portions respectively disposed inwardly of said outermost longitudinal edges in the x-direction; and a pair of elongate inner elastic laminate portions respectively disposed inwardly of said outer elastic portions in the x-direction, at least one of the inner elastic laminate portions being an elastic material attached to a supporting sheet, being elastically stretchable in a first direction and having an absolute contracted length $L_c$, a fully stretched absolute length $L_s$, and a maximum elongation $\epsilon$ of at least 0.6, said at least one of said inner elastic laminate portions also including a first zone having a first zone absolute contracted length, $L_{czone1}$, a first zone fully stretched absolute length $L_{szone1}$ and a maximum first zone elongation $\epsilon_{zone1}$, and a second zone having a second zone absolute contracted length $L_{czone2}$, a second zone fully stretched absolute length $L_{szone2}$ and a second zone maximum elongation $\epsilon_{zone2}$, wherein $\epsilon_{zone1}$ is less than or equal to about 50% of $\epsilon$, $\epsilon_{zone2}$ is greater than $\epsilon$, and $L_{czone1}$ and $L_{czone2}$ are each at least about 2 cm.

2. The absorbent article of claim 1, wherein said at least one of said inner elastic laminate portions includes a third zone positioned such that the first zone is between the second zone and the third zone, the third zone having a third zone maximum elongation $\epsilon_{zone3}$ that is greater than $\epsilon$.

3. The absorbent article of claim 1, wherein the article has a crotch region between said first waist region and said second waist region, the first zone being positioned in the crotch region of the article.

4. The absorbent article of claim 1, further comprising a diaper, the diaper including at least two of the components that are a leg cuff or barrier cuff of the diaper.

5. The absorbent article of claim 1, wherein the supporting sheet is a nonwoven laminate including one or more spunbond nonwoven layers and one or more meltblown nonwoven layers.

6. The absorbent article of claim 1, wherein said at least one of said inner elastic laminate portions has a force profile such that it has a first load force at 200% elongation of 1.6 N or less, and a second unload force at 200% elongation of 0.5 N or more.

7. A disposable absorbent article, the absorbent article comprising:
   a. a first waist region;
   b. a second waist region;
   c. a pair of outermost longitudinal edges connecting the first waist region and the second waist region;
   d. a pair of elongate outer elastic portions, respectively disposed inwardly of said outermost longitudinal edges in the x-direction; and
   e. a pair of elongate inner elastic laminate portions respectively disposed inwardly of said outer elastic portions in the x-direction, at least one of the inner elastic laminate portions being an elastic material attached to a supporting sheet and having a fully stretched absolute length $L_s$, an absolute contracted length $L_c$, and a maximum elongation $\epsilon$ of at least 0.6, said at least one inner elastic laminate portion also including a first zone having a first zone absolute contracted length $L_{czone1}$, a first zone fully stretched absolute length $L_{szone1}$ and a maximum first zone elongation $\epsilon_{zone1}$, and a second zone having second zone absolute contracted length $L_{czone2}$, a second zone fully stretched absolute length $L_{szone2}$ and a second zone maximum elongation $\epsilon_{zone2}$, wherein $\epsilon_{zone1}$ is less than or equal to about 50% of $\epsilon$, $\epsilon_{zone2}$ is greater than $\epsilon$, and $L_{czone1}$ and $L_{czone2}$ are each at least about 2 cm;
   said at least one elastic laminate portion, when in the partially stretched state such that its elongation is equal to about 0.5, having wrinkles with an average wrinkle height $H_w$ and/or a wrinkle density $D_w$, the first zone having no wrinkles or wrinkles with a first zone average wrinkle height $H_{wzone1}$ and/or a first zone wrinkle density $D_{wzone1}$, wherein $H_{wzone1}$ is zero or less than about 50% of $H_w$ and/or $D_{wzone1}$ is zero or less than about 50% of $D_w$.

8. A disposable absorbent article, the disposable absorbent article comprising:
   a first waist region, a crotch region and a second waist region; and
   a pair of elongate elastic laminate portions having lengths extending from said first waist region, through said crotch region, to said second waist region,
   wherein at least one of said elastic laminate portions comprises an elastic material attached to a supporting sheet and is elastically stretchable along its length, and has a contracted length $L_c$, a fully stretched length $L_s$, and a maximum elongation $\epsilon$ of at least 0.6, said also comprises a first zone having a first zone contracted length $L_{czone1}$, a first zone fully stretched length $L_{szone1}$ and a maximum first zone elongation $\epsilon_{zone1}$, and a second zone having a second zone contracted length $L_{czone2}$, a second zone fully stretched length $L_{szone2}$ and a maximum second zone elongation $\epsilon_{zone2}$, wherein $\epsilon_{zone1}$ is less than or equal to about 50% of $\epsilon$, $\epsilon_{zone2}$ is greater than $\epsilon$, and $L_{czone1}$ and $L_{czone2}$ are each at least about 2 cm.

* * * * *

UNITED STATES PATENT AND TRADEMARK OFFICE
CERTIFICATE OF CORRECTION

| | | |
|---|---|---|
| PATENT NO. | : 7,654,993 B2 | Page 1 of 1 |
| APPLICATION NO. | : 11/582189 | |
| DATED | : February 2, 2010 | |
| INVENTOR(S) | : Arizti et al. | |

It is certified that error appears in the above-identified patent and that said Letters Patent is hereby corrected as shown below:

On the Title Page:

The first and sole Notice should read --

Subject to any disclaimer, the term of this patent is extended or adjusted under 35 U.S.C. 154(b) by 103 days.

Column 11
Line 29, delete "$H_{zone1}$" and insert --$H_{wzone1}$--.

Signed and Sealed this

Twenty-eighth Day of September, 2010

David J. Kappos
*Director of the United States Patent and Trademark Office*